United States Patent
Teshigahara et al.

(10) Patent No.: US 7,262,148 B2
(45) Date of Patent: Aug. 28, 2007

(54) CATALYST FOR PRODUCTION OF UNSATURATED ALDEHYDE AND UNSATURATED CARBOXYLIC ACID, AND PROCESS FOR ITS PRODUCTION

(75) Inventors: Isao Teshigahara, Mie (JP); Nariyasu Kanuka, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/033,271

(22) Filed: Jan. 12, 2005

(65) Prior Publication Data

US 2005/0159620 A1    Jul. 21, 2005

Related U.S. Application Data

(63) Continuation of application No. PCT/JP04/13456, filed on Sep. 15, 2004.

(30) Foreign Application Priority Data

Dec. 3, 2003   (JP)   ............... 2003-405073

(51) Int. Cl.
  *B01J 27/06*  (2006.01)
  *B01J 23/00*  (2006.01)
  *B01J 23/58*  (2006.01)
  *B01J 23/74*  (2006.01)

(52) U.S. Cl. ............... 502/224; 502/311; 502/321; 502/330; 502/337; 502/338

(58) Field of Classification Search ............... 502/224, 502/311–321, 330, 337, 338
See application file for complete search history.

(56) References Cited

U.S. PATENT DOCUMENTS 4,052,450 A * 10/1977 Krabetz et al. ............. 562/546

2003/0162997 A1 * 8/2003 Uhara et al. ............. 562/532

FOREIGN PATENT DOCUMENTS

| EP | 0 450 596 | * | 10/1991 |
| EP | 0 756 894 | * | 7/1996 |
| JP | 53-5632 | | 3/1978 |
| JP | 55-36384 | | 9/1980 |
| JP | 56-28180 | | 6/1981 |
| JP | 56-95339 | | 8/1981 |
| JP | 57-119837 | | 7/1982 |
| JP | 6-7924 | | 2/1994 |
| JP | 2003-10695 | | 1/2003 |
| JP | 2003-010695 | * | 1/2003 |
| JP | 2003-238477 | * | 8/2003 |

* cited by examiner

*Primary Examiner*—J. A. Lorengo
*Assistant Examiner*—Patricia L. Hailey
(74) *Attorney, Agent, or Firm*—Oblon, Spivak, McClelland, Maier & Neustadt, P.C.

(57) ABSTRACT

A catalyst for producing from an olefin the corresponding unsaturated aldehyde and unsaturated carboxylic acid in good yield, and a process for its production, are presented.

It is a composite oxide catalyst containing at least molybdenum, bismuth and iron, to be used at the time of gas phase catalytic oxidation of an olefin with a molecular oxygen-containing gas to produce the corresponding unsaturated aldehyde and unsaturated carboxylic acid, wherein the loss on drying of the contained moisture, as represented by the following formula (1) (wherein $W_1$ represents the weight when the catalyst is heated for two hours at $110\pm5°$ C., and $W_2$ represents the weight of the catalyst prior to such heating), is at most 0.5 wt %:

$$\text{Loss on drying} = (W_2 - W_1)/W_2 \times 100. \quad (1)$$

7 Claims, No Drawings

CATALYST FOR PRODUCTION OF UNSATURATED ALDEHYDE AND UNSATURATED CARBOXYLIC ACID, AND PROCESS FOR ITS PRODUCTION

TECHNICAL FIELD

The present invention relates to a composite oxide catalyst for gas phase catalytic oxidation of an olefin with a molecular oxygen-containing gas to produce the respectively corresponding unsaturated aldehyde and unsaturated carboxylic acid, whereby the corresponding unsaturated aldehyde and unsaturated carboxylic acid can be produced in good yield, and a process for its production and a method for its storage.

BACKGROUND ART

Heretofore, various proposals have been made with respect to catalysts for gas phase catalytic oxidation of propylene with molecular oxygen to produce acrolein and acrylic acid, and catalysts for gas phase catalytic oxidation of isobutylene with a molecular oxygen-containing gas to produce methacrolein and methacrylic acid.

These catalysts are, of course, required to be able to produce the corresponding unsaturated aldehyde and unsaturated carboxylic acid in good yield, but also required to have sufficiently high mechanical strength and durability durable for industrial use for a long period of time.

Heretofore, in order to improve the performance of the catalyst to be used for such a reaction, it has been proposed to control the specific surface area, average pore radius, or pore volume, etc. of the catalyst within specific ranges. For example, patent document 1 proposes to control the specific surface area of a catalyst to be from 100 to 250 m$^2$/g; patent document 2 proposes to control the pore volume to be from 0.2 to 0.4 ml/g and the average pore radius to be 2000 Å; and patent document 3 proposes to control the specific surface area to be from 5 to 20 m$^2$/g, the average pore diameter to be from 0.1 to 0.9 μm and the pore volume to be from 0.3 to 0.9 ml/g.

Further, it has been proposed to improve the performance or the mechanical strength of the catalyst by controlling the conditions for drying or calcination in the production of the catalyst. For example, patent document 4 or patent document 5 proposes to carry out calcination at a temperature of from 550 to 750° C. stepwisely, or to carry out multi-stage calcination by preliminarily carrying out preparatory calcination and further carrying out the main calcination.

By such prior art, certain effects can be obtained, but they are not necessarily satisfactory. Accordingly, a new catalyst which is capable of easily improving the performance of the catalyst and which is excellent in reproducibility, and a process for its production, are still desired.

Patent Document 1: JP-B-53-5632
Patent Document 2: JP-B-6-7924
Patent Document 3: JP-A-57-119837
Patent Document 4: JP-B-55-36384
Patent Document 5: JP-B-56-28180

DISCLOSURE OF THE INVENTION

Problems to be Solved by the Invention

In view of the above described prior art, it is an object of the present invention to provide a catalyst which is capable of oxidizing an olefin by gas phase catalytic oxidation with a molecular oxygen-containing gas to advantageously produce the respectively corresponding unsaturated aldehyde and unsaturated carboxylic acid in good yield with good reproducibility, and a process for its production.

Means to Solve the Problems

The present inventors have conducted an extensive research to solve the above problems and have found that with respect to a composite oxide catalyst containing at least molybdenum, bismuth and iron, to be used for producing an unsaturated aldehyde and unsaturated carboxylic acid, the amount of moisture contained in the catalyst during the production or storage of the catalyst, is largely influential over the characteristics such as the activity, selectivity, etc. of the catalyst, and it is possible to solve the above problems by controlling the amount of moisture within a proper range.

Namely, by the study made by the present inventors, it has been found that a catalyst to provide good yield of the desired unsaturated aldehyde and unsaturated carboxylic acid, can be obtained by controlling the amount of moisture contained, to a level of at most 0.5 wt % as the loss on drying of the catalyst during the production or storage of the composite oxide catalyst containing at least molybdenum, bismuth and iron, as will be seen in Examples and Comparative Examples given hereinafter.

The above loss on drying of the catalyst is a numerical value to be obtained in accordance with method L of JIS R9301-3-1. It has been found that if this loss on drying is larger than 0.5 wt %, the activity and the selectivity in the intended reaction tend to be low, and a molded product of the catalyst having constant characteristics tends to be hardly obtainable, although the cause is not clearly understood.

Thus, the present invention resides in constructions having the following characteristics.

(1) A composite oxide catalyst for the production of an unsaturated aldehyde and an unsaturated carboxylic acid, which is a composite oxide catalyst containing at least molybdenum, bismuth and iron, to be used at the time of gas phase catalytic oxidation of an olefin with a molecular oxygen-containing gas to produce the corresponding unsaturated aldehyde and unsaturated carboxylic acid, characterized in that the loss on drying of the contained moisture, as represented by the following formula (1), is at most 0.5 wt %:

$$\text{Loss on drying} = (W2 - W1)/W2 \times 100 \quad (1)$$

(wherein W1 represents the weight when the catalyst is heated for two hours at 110±5° C., and W2 represents the weight of the catalyst prior to such heating.)

(2) The composite oxide catalyst according to (1), characterized in that the catalyst is represented by the following formula (2):

$$Mo_a Bi_b Co_c Ni_d Fe_e X_f Y_g Z_h Q_i Si_j O_k \quad (2)$$

(wherein X is at least one member of Na, K, Rb, Cs and Tl, Y is at least one member of B, P, As and W, Z is at least one member of Mg, Ca, Zn, Ce and Sm, Q is a halogen atom, and a to k represent atomic ratios of the respective elements, and when a=12, $0.5 \leq b \leq 7$, $0 \leq c \leq 10$, $0 \leq d \leq 10$, $1 \leq c+d \leq 10$, $0.05 \leq e \leq 3$, $0.0005 \leq f \leq 3$, $0 \leq g \leq 3$, $0 \leq h \leq 1$, $0 \leq i \leq 0.5$, and $0 \leq j \leq 40$, and k is a value which satisfies the oxidized states of other elements.)

(3) The composite oxide catalyst according to (1) or (2), characterized in that the olefin is propylene, and the unsaturated aldehyde and unsaturated carboxylic acid are acrolein and acrylic acid, respectively.

(4) A process for producing the composite oxide catalyst as defined in any one of (1) to (3), characterized in that the relative humidity, as calculated at 25° C., of the atmospheric gas during the temperature lowering at the time of calcination a dried product of a mixed solution or aqueous slurry containing catalyst components, is adjusted to be at most 30%.

(5) A process for producing the composite oxide catalyst as defined in any one of (1) to (3), characterized in that the relative humidity, as calculated at 25° C., of the atmospheric gas at the time of recovering the calcined product after calcination a dried product of a mixed solution or aqueous slurry containing catalyst components, is adjusted to be at most 30%.

(6) A method for storing the composite oxide catalyst as defined in any one of (1) to (3), characterized in that the relative humidity, as calculated at 25° C., of the atmospheric gas at the time of storing the catalyst, is adjusted to be at most 30%.

Effects of the Inventions

According to the process of the present invention, it is possible to provide a catalyst which has high activity and high selectivity and which provides a constant performance for a long period of time, to be used for gas phase catalytic oxidation of an olefin with a molecular oxygen-containing gas to produce the respectively corresponding unsaturated aldehyde and unsaturated carboxylic acid, on the basis of a new concept such that with respect to a composite oxide catalyst containing at least molybdenum, bismuth and iron, the amount of moisture contained in the catalyst is controlled during the production or storage of the catalyst.

BEST MODE FOR CARRYING OUT THE INVENTION

The catalyst to be provided by the present invention, is a composite oxide catalyst containing at least molybdenum, bismuth and iron. It is not particularly limited so long as it is a composite oxide catalyst containing such three components. However, a catalyst represented by the following formula (2) is particularly preferred.

$Mo_aBi_bCo_cNi_dFe_eX_fY_gZ_hQ_iSi_jO_k$ (2)

In the above formula (2), Mo represents molybdenum, Bi bismuth, Co cobalt, Ni nickel, Fe iron, Si silicon and O oxygen, and X, Y, Z, Q, a, b, c, d, e, f, g, h, i and j are as defined above. Q is particularly preferably a chlorine atom.

For the catalyst having the above composition of the present invention, the required amounts of raw material compounds containing the respective element components are suitably dissolved or dispersed in an aqueous medium to obtain a mixed solution or aqueous slurry containing the catalyst components. The raw materials for the respective catalyst components may, for example, be nitrates, ammonium salts, hydroxides, oxides, sulfates, carbonates, halides or acetates of the respective elements. For example, for molybdenum, ammonium paramolybdate, molybdenum trioxide or molybdenum chloride may, for example, be used. To the aqueous medium, a non-aqueous solvent such as an alcohol may be added in order to adjust the viscosity, as the case requires.

The mixed solution or aqueous slurry containing the catalyst components, is preferably heated to carry out a constant temperature control, and it is preferably thoroughly stirred and mixed in order to prevent localization of each component. After stirring thoroughly, the mixed solution or aqueous slurry is preferably heated at a temperature of from 100 to 350° C. for from 0.1 second to 24 hours for drying, to obtain a dried product. The drying method and the state of the dried product thereby obtained are not particularly limited. For the drying method, a spray dryer, slurry dryer or drum dryer may, for example, be used to obtain a powdery dried product, or a box type dryer or tunnel type heating furnace may be employed to obtain a block-shaped dried product. The obtained dried product may be calcined as it is, but it is preferred that after pulverization as the case requires, it is molded into a desired shape and size, followed by calcination.

As the molding method of the above dried product, an optional molding method may be employed such as extrusion molding, granulation molding or tabletting. The shape, size, etc. of the molded product are not particularly limited, and they may suitably be selected from conventional shapes, sizes, etc. For example, the shape may be any shape such as a spherical, cylindrical or ring-shape. The size is preferably such that the longest diameter is from 3 to 15 mm.

At the time of the above molding, in order to improve the mechanical strength or degradation of the molded product, commonly known inorganic fibers such as glass fibers, various whiskers, etc. may be used. Further, in order to control the physical properties of the catalyst with good reproducibility, an additive which is commonly known as a binder, such as ammonium nitrate, cellulose, starch, polyvinyl alcohol or stearic acid, may also be used.

In the present invention, the above composite oxide catalyst may be used in the form of a catalyst supported on a carrier. As the carrier, a commonly known carrier such as alumina, silica, silica/alumina, silicon carbide, titanium oxide, magnesium oxide, aluminum sponge or silica/titania, may widely be used. Also when such a supported catalyst is to be produced, the above-mentioned inorganic fibers, etc. may be added in order to improve the mechanical strength, etc., or the above-mentioned binder may be used in order to control the physical properties of the catalyst with good reproducibility.

In the present invention, the molded product of the dried product containing the catalyst components thus obtained, is then calcined. The calcination is preferably carried out in the presence of an oxygen-containing gas preferably at from 400 to 650° C., particularly preferably at from 450 to 600° C., preferably for from one minute to 24 hours, particularly preferably for from 10 minutes to 10 hours.

In the present invention, an atmospheric calcining furnace may be employed for the above calcination. As such an atmospheric calcining furnace, there may, for example, be employed a method wherein the catalyst is packed in a fixed bed reactor and heating is carried out from the exterior under an atmospheric gas stream, a method wherein the above fixed bed reactor is of a heat exchange type, a method wherein an atmospheric gas is fed into the interior of a muffle furnace, a method wherein an atmospheric gas is fed into the interior of a tunnel furnace, or a method wherein an atmospheric gas is fed into the interior of the kiln furnace. Taking the efficiency for control of the atmospheric gas flow rate into consideration, it is preferred to employ a method wherein the catalyst is packed in a fixed bed reactor and heating is carried out from the exterior under an atmospheric gas stream, more preferably a method wherein the catalyst is packed into a heat exchange type fixed bed reactor, and heating is carried out from the exterior under an atmospheric gas stream. As the atmospheric gas stream, not only air, but a mixed gas of inert gasses, such as air and nitrogen, may be employed. From the economical advantage, it is preferred to employ air.

In the present invention, in order to control the amount of moisture contained in the catalyst to a level of at most 0.5 wt % as the loss on drying of the catalyst, as mentioned above, it is usually preferred to reduce the relative humidity of the atmospheric gas to be used for calcination, by carrying out e.g. elimination of moisture. Further, it is preferred that at the time of temperature lowering of the calcinated catalyst after carrying out the calcination under an atmospheric gas stream, the relative humidity of the atmospheric gas during the temperature lowering, is controlled to be within a prescribed range. Thus, the relative humidity at 25° C. of the atmospheric gas during the temperature lowering, is preferably at most 30%, more preferably at most 20%, further preferably at most 10%. If the above relative humidity of the atmospheric gas during the temperature lowering is higher than 30%, it may happen that at the time of taking out the catalyst from the calcining furnace after the temperature lowering, the moisture content of the catalyst tends to increase, and the loss on drying of the catalyst tends to be higher than 0.5 wt %.

Further, in the present invention, in an operation of withdrawing and recovering the catalyst from the calcining furnace, the atmospheric gas which is in contact with the catalyst, preferably has a relative humidity of at most 30% at 25° C. If this relative humidity of the atmospheric gas is higher than 30%, when the operation takes a long time, there may be a case where the moisture content of the catalyst increases, and the loss on drying of the catalyst will be higher than 0.5 wt %.

Further, in the present invention, it is preferred to control the relative humidity at 25° C. of the atmospheric gas during the storage of the catalyst calcined as described above to be at most 30%. If the relative humidity of the atmospheric gas during the storage of the catalyst is higher than 30%, there may be a case where the moisture content of the catalyst increases, and the loss on drying of the catalyst will be higher than 0.5 wt %. In order to store the catalyst while controlling the relative humidity to a level of at most 30%, a desiccator, an autodryer or the like may be employed. Thus, by storing the catalyst having a loss on drying of at most 0.5% as sealed in e.g. a polymer bag, a resin container or a storage can, to shut out water vapor, it is possible to suitably maintain the loss on drying to be at most 0.5 wt %.

Thus, the catalyst of the present invention is required to have a loss on drying being at most 0.5 wt %. If the loss on drying exceeds 0.5 wt %, the yield of the desired unsaturated aldehyde and unsaturated carboxylic acid tends to decrease, as mentioned above. Especially, in the present invention, the loss on drying is preferably at most 0.3 wt %, particularly preferably from 0.01 to 0.2 wt %. On the other hand, the loss on drying may be less than 0.01 wt % without any particular problem from the viewpoint of performance of the catalyst, but an installation cost to attain such a level, will be large, such being economically disadvantageous. Here, the loss on drying of the catalyst is a numerical value obtained in accordance with method L of JIS R9301-3-1. Namely, it is obtained by the following formula (1) wherein W1 is the weight after the catalyst is heated at 110±5° C. for two hours, and W2 is the weight of the catalyst before the heating.

Loss on drying=$(W2-W1)/W2 \times 100$    (1)

The specific surface area, the average pore diameter and the pore volume, which the composite oxide catalyst of the present invention may have, are not particularly limited and may be within the ranges of those, which conventional catalysts may have. However, the specific surface area is preferably from 5 to 25 m²/g, the average pore diameter is preferably from 0.03 to 1 μm, and the pore volume is preferably from 0.2 to 0.7 cc/g.

In the present invention, the means for gas phase oxidation of an olefin by using the above catalyst and by using molecular oxygen or a molecular oxygen-containing gas, to produce the respectively corresponding unsaturated aldehyde and unsaturated carboxylic acid, may be a conventional means. For example, as the reactor, a fixed bed tubular reactor may be employed. In such a case, the reaction may be a single flow process through the reactor, or may be a recycle process, and it may be carried out under such conditions as commonly employed in a reaction of this type.

For example, a mixed gas comprising from 1 to 15 vol % of propylene, from 3 to 30 vol % of molecular oxygen, from 0 to 60 vol % of steam, from 20 to 80 vol % of an inert gas such as nitrogen or carbon dioxide gas, etc., is introduced to a catalyst layer having the catalyst packed in each reactor having an internal diameter of preferably from 15 to 50 mm at a temperature of from 250 to 450° C. under a pressure of from 0.1 to 1 MPa at a space velocity (SV) of from 300 to 5000 hr$^{-1}$. Otherwise, in the present invention, in order to increase the productivity, the operation may be made under a higher load reaction condition, such as a higher raw material concentration or a higher space velocity.

EXAMPLES

Now, the present invention will be described in further detail with reference to Examples of the present invention. However, it should be understood that the present invention is by no means restricted to such Examples. In the following, the conversion, the selectivity and the yield are calculated by the following formulae. Further, the relative humidity is one at 25° C.

Conversion of propylene (mol %)=(mols of reacted propylene/mols of supplied propylene)×100

Yield of acrolein (mol %)=(mols of formed acrolein)/(mols of supplied propylene)×100

Yield of acrylic acid (mol %)=(mols of formed acrylic acid)/(mols of supplied propylene)×100

Example 1

105.5 g of ammonium paramolybdate was dissolved in 500 ml of heated pure water. Then, 10.1 g of ferric nitrate, 48.5 g of nickel nitrate and 48.5 g of cobalt nitrate were dissolved in 100 ml of heated pure water. These solutions were gradually mixed with sufficient stirring to obtain a slurry.

Then, 0.96 g of borax and 0.51 g of potassium nitrate were dissolved in 40 ml of pure water under heating and added to the above slurry. Then, 72.9 g of silica was added and thoroughly stirred. Then, 2.7 ml of nitric acid was added to 20 ml of pure water and 24.1 g of bismuth nitrate was further added and mixed with stirring.

This slurry was heated and dried and then subjected to thermal treatment in an air atmosphere at 300° C. for one hour. The obtained granular solid was pulverized and molded by a tabletting machine into tablets having a diameter of 5 mm and a height of 4 mm.

Then, the molded product was packed into a heat exchange type fixed bed reactor, and as the atmospheric gas, air having a relative humidity of at most 20% at a temperature of 25° C., was fed. Heating was carried out from the exterior to carry out calcination at 505° C. for 4 hours. It was cooled to room temperature under the air stream having a relative humidity of at most 20% at a temperature of 25° C. The catalyst was recovered in an environment of a relative humidity of from 20 to 30%, to obtain a composite oxide catalyst. The catalyst calculated from the raw materials charged, is a composite oxide having the following atomic ratio.

Mo:Bi:Ni:Co:Fe:Na:B:K:Si=12:1:3.3:3.3:0.6:0.1:0.2: 0.1:24

The loss on drying of the obtained composite oxide catalyst was 0.18 wt %.

20 ml of this catalyst was packed into a stainless steel reactor equipped with a niter jacket and having an inner diameter of 15 mm, and a feed gas having a propylene concentration of 10%, a steam concentration of 17% and an air concentration of 73%, was passed therethrough at a reaction temperature of 315° C. under atmospheric pressure for a contact time of 2.0 seconds to carry out an oxidation reaction of propylene. The results are shown in Table 1.

Comparative Example 1

In Example 1, after the calcination, after cooling to 100° C. under the air stream having a relative humidity of 20% at a temperature of 25° C., the calcining reactor was opened, and the catalyst was left to cool overnight in an environment having a relative humidity of from 60 to 80% at a temperature of 25° C. Then, it was taken out in an environment having a relative humidity of from 60 to 80% at a temperature of 25° C. Otherwise, in the same manner as in Example 1, a composite oxide catalyst was prepared.

The loss on drying of the obtained catalyst was 0.91%. Further, using the catalyst, an oxidation reaction of propylene was carried out in the same manner as in Example 1, and the results are shown in Table 1.

Comparative Example 2

The catalyst obtained in Example 1 was stored for 24 hours in an atmosphere having a relative humidity of from 90 to 98% at a temperature of 25° C. The loss on drying of the obtained catalyst was 1.7%. Using the catalyst, an oxidation reaction of propylene was carried out in the same manner as in Example 1, and the results are shown in Table 1.

TABLE 1

|  | Loss on drying (wt %) | Conversion of propylene (mol %) | Yield of acrolein (mol %) | Yield of acrylic acid (mol %) | Total yield (mol %) |
|---|---|---|---|---|---|
| Ex. 1 | 0.18 | 98.5 | 90.1 | 4.2 | 94.3 |
| Comp. Ex. 1 | 0.91 | 97.7 | 90.5 | 2.9 | 93.4 |
| Comp. Ex. 2 | 1.7 | 97.4 | 89.0 | 3.8 | 92.8 |

INDUSTRIAL APPLICABILITY

A catalyst produced by the process of the present invention, is useful for gas phase catalytic oxidation of an olefin with a molecular oxygen-containing gas to produce the corresponding unsaturated aldehyde and unsaturated carboxylic acid. The produced unsaturated aldehyde and unsaturated carboxylic acid may be used in a wide range of applications as e.g. starting materials for various chemical products, monomers for common resins, monomers for functional resins such as water absorptive resins, flocculating agents or thickeners.

The entire disclosure of Japanese Patent Application No. 2003-405073 filed on Dec. 3, 2003 including specification, claims and summary is incorporated herein by reference in its entirety.

What is claimed is:

1. A process for producing a composite oxide catalyst, comprising:

conducting cooling of a calcined dried product of a mixed solution or aqueous slurry containing catalyst components under a gaseous atmosphere having a relative humidity, as calculated at 25° C., of at most 30%;

wherein said composite oxide catalyst comprises molybdenum, bismuth and iron, for the production of an unsaturated aldehyde and an unsaturated carboxylic acid, for use in the gas phase catalytic oxidation of an olefin with a molecular oxygen-containing gas to produce the corresponding unsaturated aldehyde and unsaturated carboxylic acid, whereupon, having prepared the composite oxide catalyst, having calcined the catalyst in a furnace under an atmosphere having a relative humidity, as determined at 25° C., of at most 30% and having withdrawn and recovered the calcined catalyst from the furnace and having stored the calcined catalyst, all under an atmosphere of a relative humidity of at most 30%, and then upon drying the stored catalyst, the loss of moisture upon drying is at most 0.5 wt % as determined by the equation (1):

$$\text{Loss on drying} = (W2-W1)/W2 \times 100 \tag{1}$$

wherein W1 represents the weight when the catalyst is heated for two hours at 110±5° C., and W2 represents the weight of the catalyst prior to said heating.

2. The process for producing the composite oxide catalyst as defined in claim 1, comprising conducting the cooling of the calcined dried product under a gaseous atmosphere having a relative humidity of at most 20%.

3. The process for producing the composite oxide catalyst as defined in claim 1, comprising recovering said cooled calcined product under a gaseous atmosphere having a relative humidity, as calculated at 25° C., of at most 30%.

4. The process for producing the composite oxide catalyst as defined in claim 3, comprising storing the recovered composite oxide catalyst under a gaseous atmosphere having a relative humidity, as calculated at 25° C., of at most 30%.

5. The process according to claim 1, wherein the catalyst has formula (2):

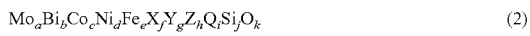

$$Mo_aBi_bCo_cNi_dFe_eX_fY_gZ_hQ_iSi_jO_k \tag{2}$$

wherein X is at least one member selected from the group consisting of Na, K, Rb, Cs and Tl, Y is at least one member selected from the group consisting of B, P, As and W, Z is at least one member selected from the group consisting of Mg, Ca, Zn, Ce and Sm, Q is a halogen atom, and a to k represent atomic ratios of the respective elements, such that when a=12, 0.5≦b≦7, 0≦c≦10, 0≦d≦10, 1≦c+d≦10, 0.05≦e≦3, 0.0005≦f≦3, 0≦g≦3, 0≦h≦1, 0≦i≦0.5, and 0≦j≦40, and k is a value which satisfies the oxidized states of the other elements of the catalyst.

6. The process according to claim 1, wherein said weight loss upon drying is at most 0.3 wt %.

7. The process according to claim 1, wherein said weight loss upon drying ranges from 0.01 to 0.2 wt %.

* * * * *